(12) United States Patent
Umemura et al.

(10) Patent No.: US 7,604,600 B2
(45) Date of Patent: Oct. 20, 2009

(54) ULTRASONIC IMAGING DEVICE

(75) Inventors: Shin-ichiro Umemura, Muko (JP);
Hiroshi Kanda, Tokorozawa (JP);
Takashi Azuma, Kawasaki (JP)

(73) Assignee: Hitachi Medical Corporation, Tokyo (JP)

( * ) Notice: Subject to any disclaimer, the term of this patent is extended or adjusted under 35 U.S.C. 154(b) by 242 days.

(21) Appl. No.: 10/546,658

(22) PCT Filed: Dec. 4, 2003

(86) PCT No.: PCT/JP03/15559

§ 371 (c)(1),
(2), (4) Date: Aug. 23, 2005

(87) PCT Pub. No.: WO2004/082483

PCT Pub. Date: Sep. 30, 2004

(65) Prior Publication Data

US 2006/0173340 A1 Aug. 3, 2006

(30) Foreign Application Priority Data

Mar. 17, 2003 (JP) .............................. 2003-071784

(51) Int. Cl.
*A61B 8/14* (2006.01)
(52) U.S. Cl. ...................... 600/458; 600/437; 600/439; 600/440; 600/443; 600/445
(58) Field of Classification Search ................. 600/458, 600/437, 439, 440, 443, 445
See application file for complete search history.

(56) References Cited

U.S. PATENT DOCUMENTS 6,095,980 A 8/2000 Burns et al.

2002/0188199 A1* 12/2002 McLaughlin et al. ........ 600/437

FOREIGN PATENT DOCUMENTS

| JP | 2001-212144 | 8/2001 |
|---|---|---|
| JP | 2002-224111 | 8/2002 |
| JP | 2002-360569 | 12/2002 |
| JP | 2003-38490 | 2/2003 |
| JP | 2003-135467 | 5/2003 |

OTHER PUBLICATIONS

V.L. Newhouse et al., "Second Harmonic Doppler Ultrasound Blood Perfusion Measurement", 1992 Ultrasonics Symposium—pp. 1175-1177.
P.J. Phillips, "Contrast Pulse Sequences (CPS): Imaging Nonlinear Microbubbles", Acuson, 2001 IEEE Ultrasonics Symposium—pp. 1739-1745.
Shin-ichiro Umemura et al., "Enhancement of Sonodynamic Tissue Damage Production by Second-Harmonic Superimposition: Theoretical Analysis of Its Mechanism", IEEE Transactions on Ultrasonics, Perroelectrics, and Frequency Control, vol. 43, No. 6, Nov. 1996—pp. 1054-1062.
"Phase-Coded Pulse Sequence For Non-Linear Imaging", Wilkening et al, IEEE Ultrasonics Symposium, 2000, pp. 1559-1562.

* cited by examiner

*Primary Examiner*—Brian Casler
*Assistant Examiner*—Baisakhi Roy
(74) *Attorney, Agent, or Firm*—Antonelli, Terry, Stout & Kraus, LLP.

(57) ABSTRACT

An ultrasonic imaging device for transmitting/receiving ultrasonic pulses to/from a living body in which microbubbles for contrast are introduced and forming a contrast image of the inside of the living body by using the microbubble for contrast, wherein transmitting/receiving operations are performed N times (N=an integer of three or greater) by using transmission pulse waves having a common envelope signal while varying carrier waves in phase by 360°/N from one wave to another under the same transmission/reception wave focus condition, and by summing N pieces of time-series reception echo signals obtained by the N times of transmitting/receiving operations to obtain a summed signal, thereby forming the contrast image.

7 Claims, 15 Drawing Sheets

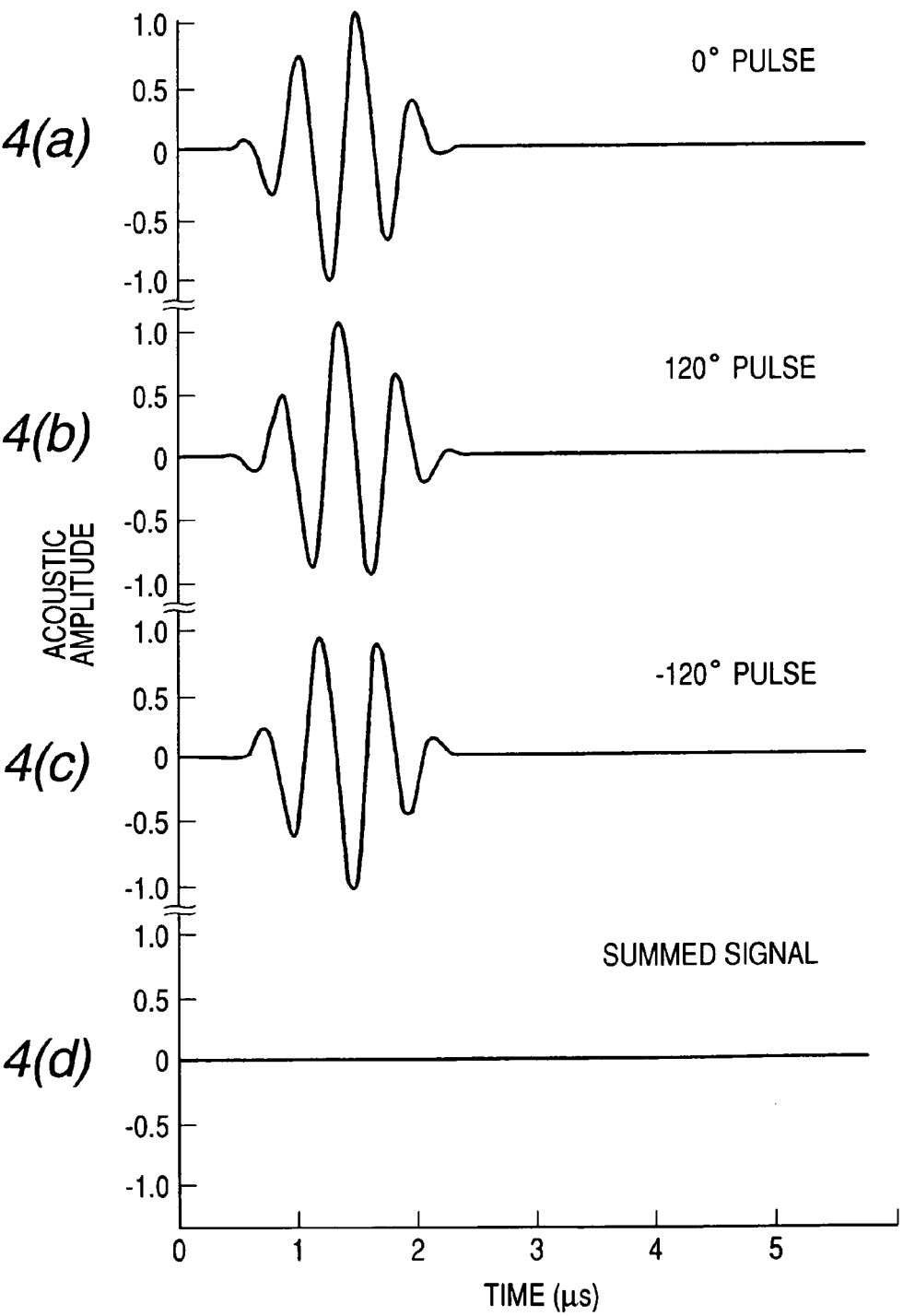

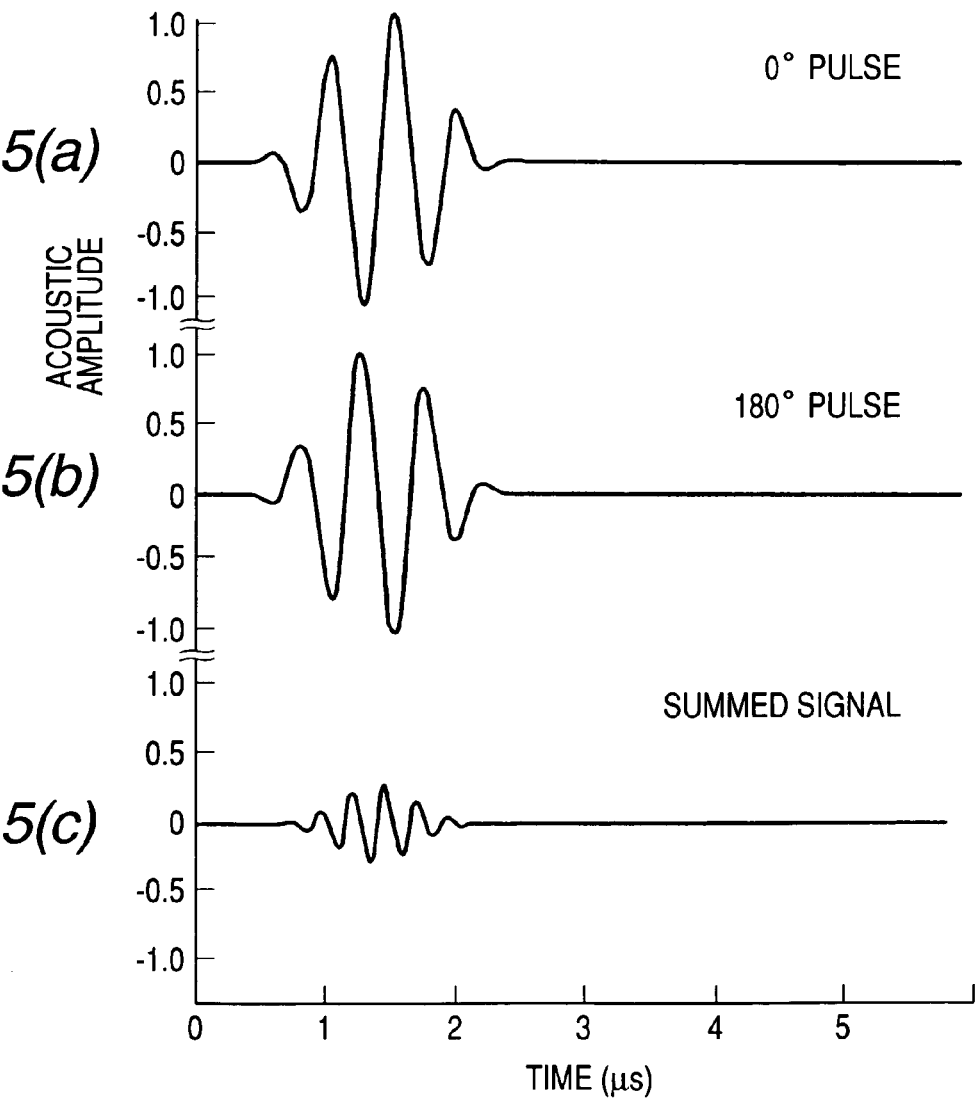
FIG. 5(a)   0° PULSE
FIG. 5(b)   180° PULSE
FIG. 5(c)   SUMMED SIGNAL

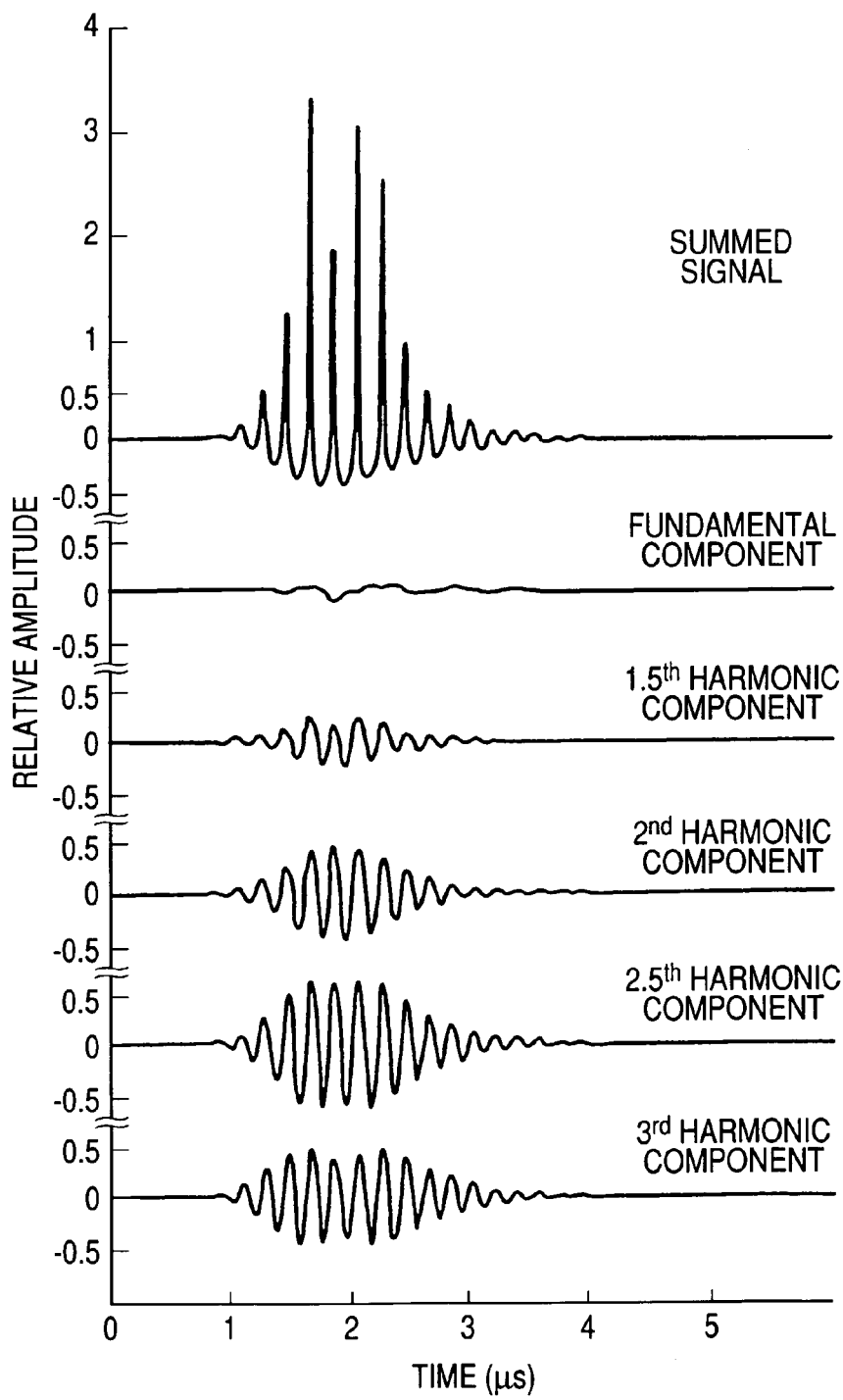
FIG. 7(a) SUMMED SIGNAL
FIG. 7(b) FUNDAMENTAL COMPONENT
FIG. 7(c) 1.5th HARMONIC COMPONENT
FIG. 7(d) 2nd HARMONIC COMPONENT
FIG. 7(e) 2.5th HARMONIC COMPONENT
FIG. 7(f) 3rd HARMONIC COMPONENT

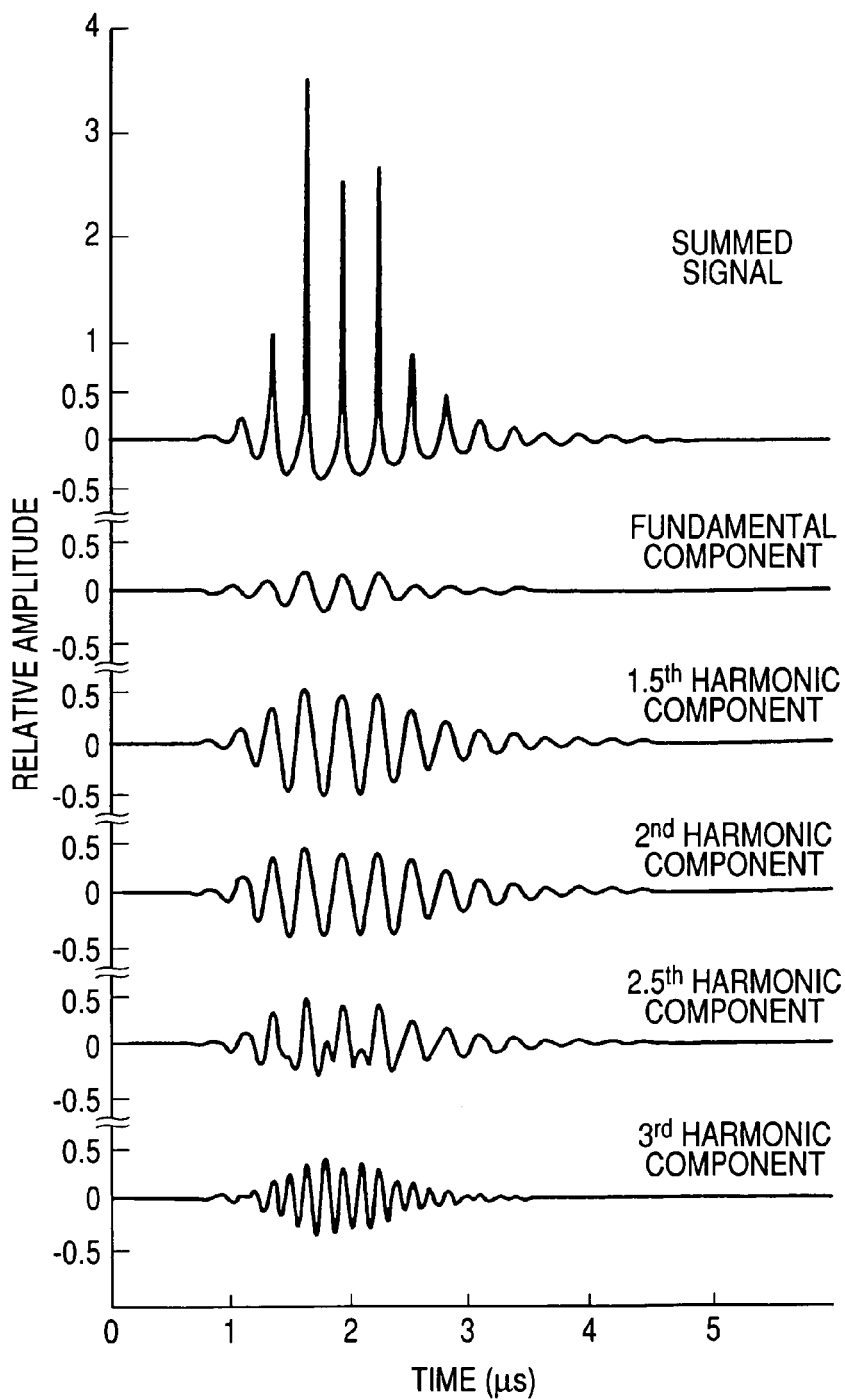
FIG. 9(a) SUMMED SIGNAL
FIG. 9(b) FUNDAMENTAL COMPONENT
FIG. 9(c) 1.5th HARMONIC COMPONENT
FIG. 9(d) 2nd HARMONIC COMPONENT
FIG. 9(e) 2.5th HARMONIC COMPONENT
FIG. 9(f) 3rd HARMONIC COMPONENT

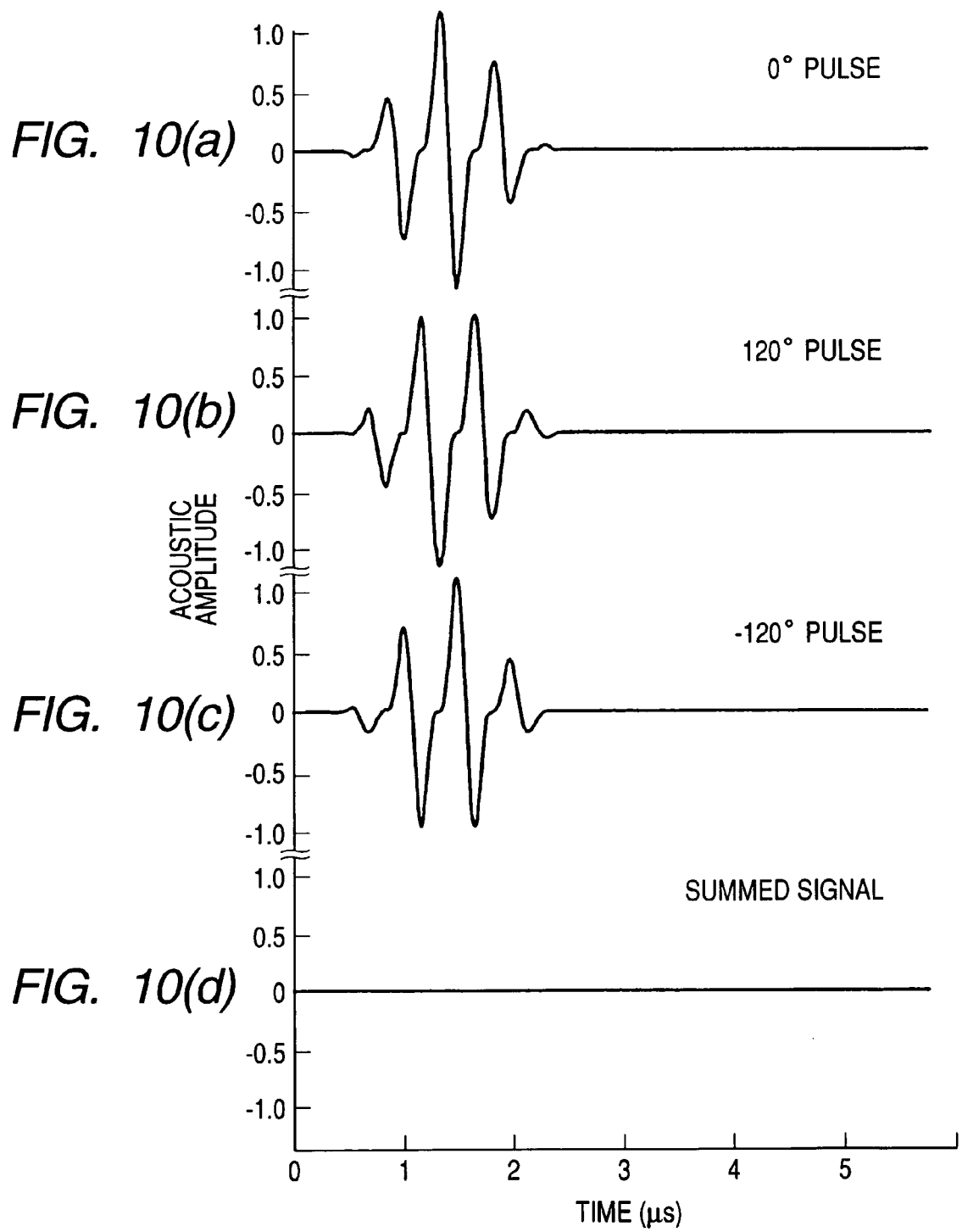

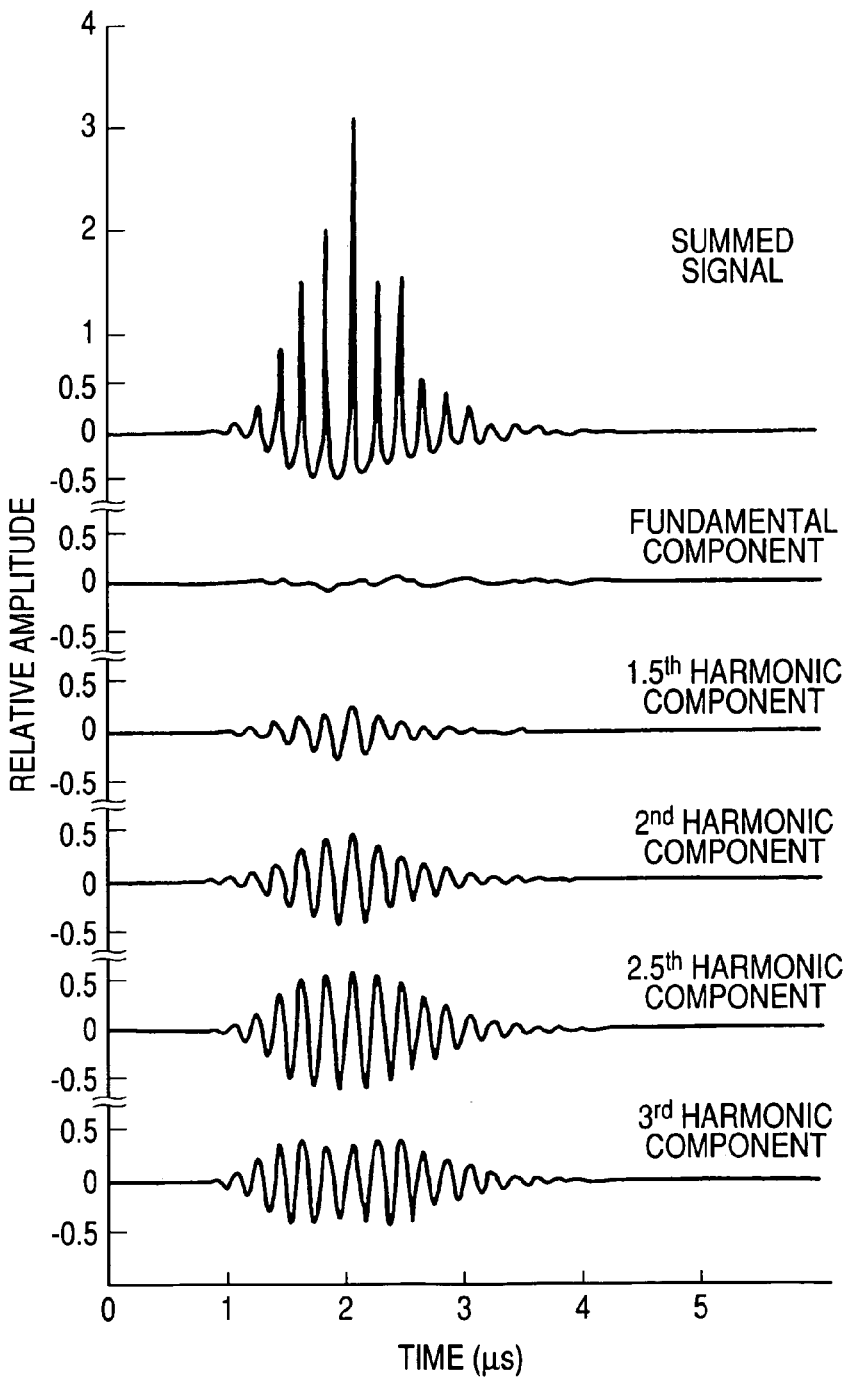
FIG. 12(a) SUMMED SIGNAL
FIG. 12(b) FUNDAMENTAL COMPONENT
FIG. 12(c) 1.5th HARMONIC COMPONENT
FIG. 12(d) 2nd HARMONIC COMPONENT
FIG. 12(e) 2.5th HARMONIC COMPONENT
FIG. 12(f) 3rd HARMONIC COMPONENT

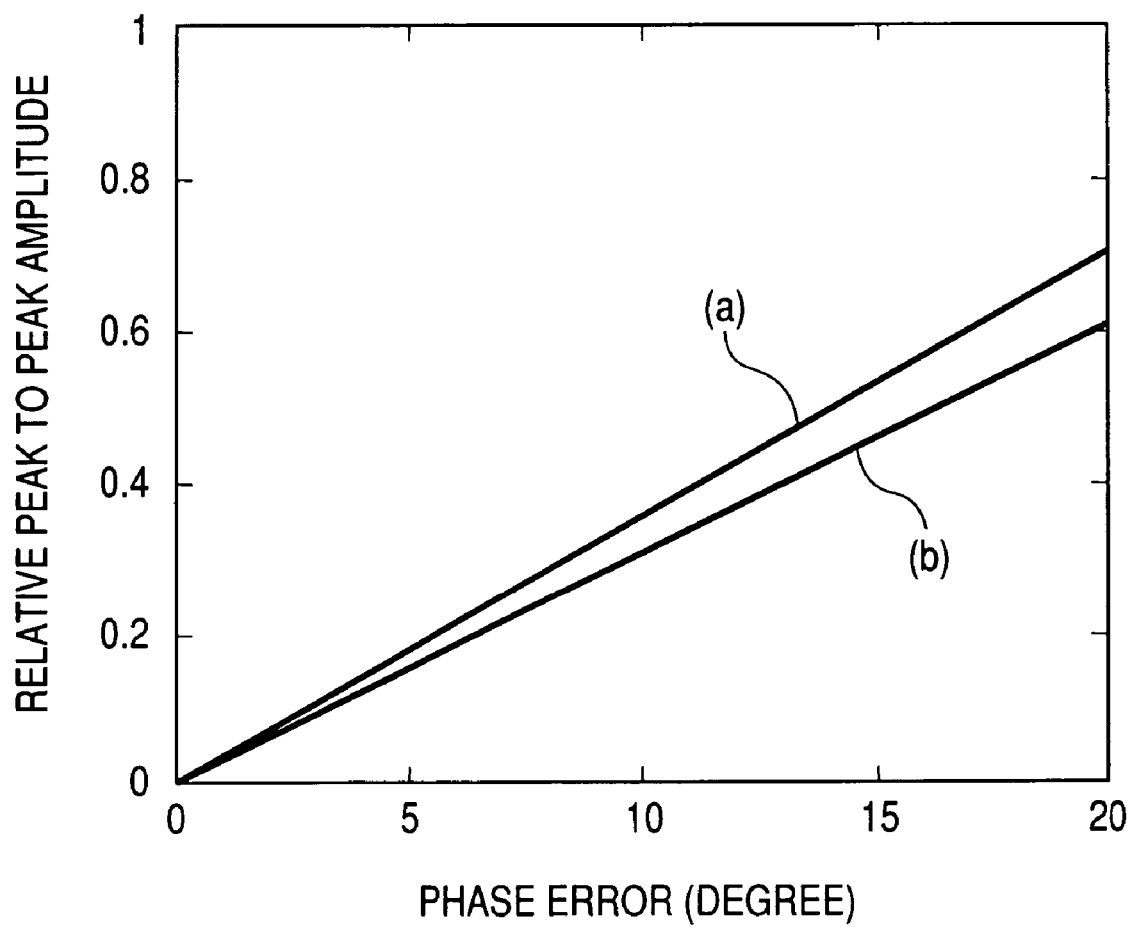

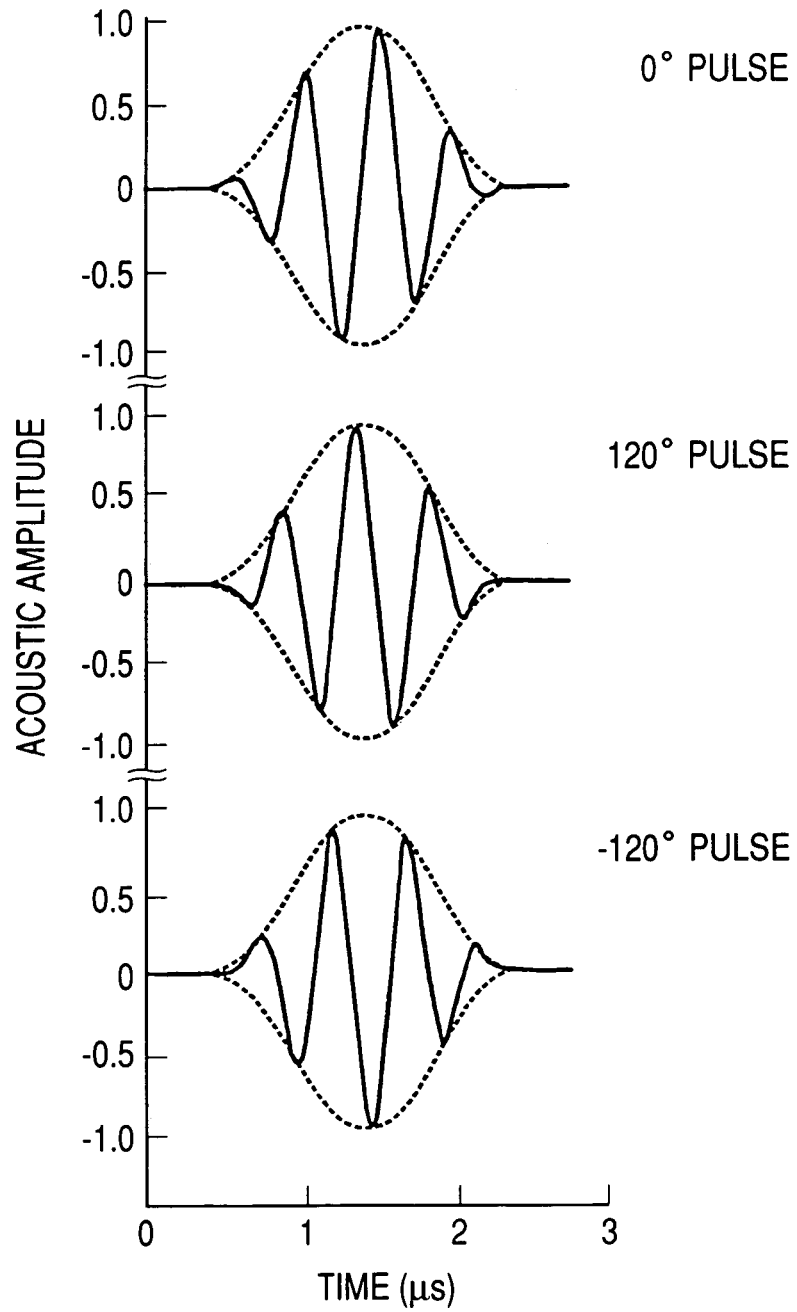
FIG. 15(a) 0° PULSE
FIG. 15(b) 120° PULSE
FIG. 15(c) -120° PULSE

ULTRASONIC IMAGING DEVICE

TECHNICAL FIELD

The present invention relates to an ultrasonic technique for transmitting/receiving ultrasonic waves to/from a living body to thereby capture an image of the inside of the living body and, more particularly, to an ultrasonic imaging technique for capturing an image by using a microbubble contrast medium.

BACKGROUND ART

An ultrasonic imaging apparatus for transmitting/receiving pulse ultrasonic waves to/from a living body to capture an image of the inside of the living body is widely used for medical diagnosis.

In the fields of X rays and MRI among image diagnosis modalities, a contrast medium has been being used for capturing an image of a blood vessel and the like. The purpose is to obtain a contrast-enhanced image of a structure and a distribution of a blood vessel system by injecting a contrast medium into blood and to carry out a diagnosis of a disease reflected in the blood vessel system such as a malignant tumor or an infarct with high accuracy.

In contrast, a contrast medium has not been widely used for ultrasonic diagnosis. In recent years, contrast media are being widely used because of appearance of a contrast medium in the form of a formulation obtained by stabilizing microbubbles in the size of the order of microns. The principle uses the phenomenon such that microbubbles each having the diameter of about 1 micron vibrate with a large amplitude in resonance with ultrasonic waves of a few MHz used for ultrasonic diagnosis, as a result, ultrasonic waves in the frequency range are scattered well, and contrast creating performance increases.

The microbubble ultrasonic contrast medium is characterized by its nonlinearity for the following reason. Microbubbles have a nature that increase in the volume when negative pressure is applied is much larger than decrease in the volume when positive pressure having the same amplitude is applied. Consequently, echo signals scattered by the microbubbles include many second harmonic components having a frequency twice as high as that of a transmission signal. V. L. Newhouse et al. have reported a method of obtaining a blood flow Doppler signal emphasized on a soft tissue on the basis of the second harmonic components for the first time in 1992 (refer to, for example, Document 1: 1992 IEEE Ultrasonics Symposium Proceedings, pp. 1175-1177).

P. N. Burns et al. have proposed a pulse inversion of performing transmitting/receiving operations twice by using a transmission acoustic pressure pulse waveform obtained by inverting the polarity and adding obtained two echo signals (refer to, for example, Document 2: U.S. Pat. No. 6,095,980). By the addition, a fundamental wave component of an echo signal from a soft tissue whose movement can be ignored is cancelled out since a signal whose phase is turned by 180° is added. However, since a signal whose phase is turned by 360° is added, a second harmonic wave component grows double by the addition. Although the necessary number of transmission times doubles, in theory, the fundamental wave component can be eliminated from the soft tissue without a band pass filter, so that a second harmonic wave echo signal having excellent distance resolution can be obtained. With respect to a scatterer whose change occurring during the twice of transmitting/receiving operations cannot be ignored like a microbubble contrast medium in the blood flow, a fundamental wave echo signal from the scatterer is not cancelled out completely. However, it rather matches the object of today of obtaining an echo image in which a contrast medium is emphasized on a soft tissue.

P. J. Phillips has proposed a method of performing transmitting/receiving operations three times while inverting the polarity of a transmission acoustic pressure pulse waveform and, simultaneously, varying the amplitude (refer to, for example, Document 3: 2001 IEEE Ultrasonics Symposium Proceedings, pp. 1739-1745). In the method, transmitting/receiving operation is performed three times while modulating the transmission amplitude like 0.5, −1, and 0.5, and echo signals obtained are added. Specifically, the same pulse waveform is used for the transmission of the first and third times, and a pulse waveform obtained by inverting the phase of the pulse waveform for the first and third times and doubling the amplitude is used for the transmission of the second time. In a manner similar to the normal pulse inversion, echo signal components from a linear scatterer whose change is slow cancel each other out, and even-number harmonic components in an echo signal, which are generated by a nonlinear scatterer and nonlinear propagation are emphasized. In addition, the method is characterized that all of components including fundamental waves out of echo signal components generated by the nonlinear scatterer and nonlinear propagation are extracted by amplification modulation. Accordingly, higher sensitivity to an echo signal by the nonlinear scatterer and nonlinear propagation than that of the normal pulse inversion is expected. The higher sensitivity is realized by using the fact that dependency of nonlinear scattering using microbubbles on an incident acoustic pressure amplitude is much larger than dependency of nonlinear propagation. By the higher sensitivity, an effect of nonlinear scattering can be detected also at a transmission acoustic pressure at which an effect of the nonlinear propagation is relatively small. Thus, as compared with normal pulse inversion, a clear distinction of a contrast medium from a soft tissue can be made more easily.

DISCLOSURE OF THE INVENTION

As described above, the conventional technique (Document 1) proposes a method of obtaining a blood flow Doppler signal emphasized on a soft tissue on the basis of the second harmonic wave component. However, the conventional technique has a problem. When only a bandpass filter is used to extract the second harmonic wave component from an echo signal, the pulse of a second harmonic wave echo signal obtained as an output signal becomes long.

The problem occurs for a reason such that, since the amplitude of a fundamental wave component included in an echo signal is larger than that of the second harmonic wave component by at least one digit, a filter having a sharp band blocking characteristic or a narrow band pass characteristic has to be used. This problem is particularly severe at the time of displaying a two-dimensional image of a blood flow since the resolution in the distance direction deteriorates.

The conventional technique (Document 2) proposes, to solve the problem, pulse inversion of performing transmitting/receiving operation twice by using transmission acoustic pressure pulse waveforms obtained by inverting the polarity and adding two echo signals derived.

The sound speed in many substances such as living body soft tissues under high pressure is higher than that under low pressure. It is known that, due to the nonlinearity, when an ultrasonic pulse propagates a soft tissue, it propagates in a portion of high acoustic pressure faster than in a portion of low acoustic pressure. As a result, during propagation, an acoustic pressure waveform which is originally a sine wave shape changes to an N wave shape that rises sharply and trails smoothly, that is, which comes to have a harmonic component such as a second harmonic wave.

When the ultrasonic pulse is scattered in a soft tissue, even if a microbubble contrast medium does not exist, an echo signal having a harmonic component returns from the soft tissue. A method of forming an echo image on the basis of the harmonic component is called tissue harmonic imaging. The tissue harmonic imaging is generally used recently because of its acoustic S/N ratio higher than that of an echo image formed on the basis of the fundamental component. However, it means that even if the pulse inversion is used, an echo signal in which a harmonic component generated by scattering with the microbubble contrast medium and a harmonic component generated by propagation of a transmission pulse are mixed is obtained, and it is difficult to perform imaging as an inherent object in which a contrast medium is clearly distinguished from a soft tissue.

The nonlinear scattering by the microbubble contrast medium tends to be observed generally also at a low acoustic pressure as compared with nonlinear propagation in a soft tissue. Consequently, a method of forming an echo image mainly by nonlinear components from the microbubble contrast medium while suppressing generation of tissue harmonic components by the pulse inversion with suppressed transmission acoustic pressure is widely employed. Under present circumstances, due to insufficient signal amplitude, it is not easy to obtain an echo image having an S/N ratio high enough to make a definite diagnosis expected for a contrast diagnosis.

As a method of solving the problem to a certain extent, a conventional technique (Document 3) proposes a method of inverting the polarity of a transmission acoustic pressure pulse waveform and, simultaneously, performing transmitting/receiving operation three times while varying the amplitude. However, the method does not eliminate a tissue harmonic echo signal generated when a transmit pulse nonlinearly propagates a soft tissue as a principle.

An object of the present invention is to provide an ultrasonic imaging technique realizing a contrast echo image having an S/N ratio high enough to make a definite diagnosis on the basis of the contrast echo image by clearly distinguishing an echo component generated when a transmit pulse is scattered by a microbubble contrast medium from a tissue harmonic component generated when the transmit pulse nonlinearly propagates and performing imaging.

To achieve the object, in the invention, transmitting/receiving operation is performed N times (N=an integer of three or greater) by using transmission pulse waves having different waveforms under the same transmission/reception wave focus condition, thereby suppressing transmission/reception sensitivity to components from a fundamental wave to the (N−1)th-order harmonic wave of an ultrasonic echo signal from a soft tissue in the living body, and transmission/reception sensitivity to an ultrasonic echo signal from the microbubbles for contrast is obtained.

Further, in the present invention, transmitting/receiving operation is performed N times (N=an integer of three or greater) by using transmission pulse waves having a common envelope signal under the same transmission/reception wave focus condition while varying the carrier waves in phase by 360°/N from one wave to the next, and N pieces of time-series reception echo signals obtained by the transmitting/receiving operation of N times are summed to obtain a summed signal, thereby forming the contrast image.

As an example, the case where N is three will be described. Transmitting/receiving operation is performed three times while commonly using an envelope signal of transmission acoustic pressure pulse waveforms, and varying the carrier waves in phase by about 120° from one wave to the next, and three echo signals obtained are summed. By the summation, the fundamental component and the second harmonic component of the echo signal scattered by a linear scatterer whose change can be ignored are cancelled out simultaneously for the following reason. When attention is paid to the phases of three echo signals from the scatterer, it is natural that the fundamental components vary in phase by about 120° from one component to another. In addition, the second harmonic components also vary in phase by about 120° from one component to another in the direction opposite to the direction in the fundamental component.

On the other hand, echo signals scattered by the contrast microbubbles as nonlinear resonators are not cancelled out. Consequently, a signal which does not contain a signal component resulted from nonlinear propagation or the like in a soft tissue but is resulted only from the microbubbles for contrast can be extracted from the echo signal.

The principle will be easily understood when a problem of vibration of a reciprocating 4-stroke in-line engine is considered. When a crankshaft rotates at constant angular velocity, linear velocity at which each of pistons constructing the reciprocating engine includes not only the fundamental component of the angular velocity but also a harmonic component of an unignorable amplitude.

The 4-stroke in-line 4-cylinder engine is usually constructed so that two sets each having two in-phase pistons symmetrically disposed form a crank angle of 180°. FIG. 1(a) shows the relation of phases of fundamental waves. With the configuration, fundamental components generated by the pistons of the sets cancel each other out. FIG. 1(b) shows the relation of phases of second harmonic waves. The second harmonic component grows double and, as a result, vibration having a frequency twice as high as the rotational speed of the crankshaft becomes an issue. In the diagram, the solid line shows the phase of vibration generated by the first piston set, and the dotted line shows the phase of vibration generated by the second piston set. The 4-cylinder engine having a balancer that rotates at an angular speed twice as high as that of the crankshaft is provided to cancel out the vibration.

On the other hand, a 4-stroke in-line 6-cylinder engine is constructed so that each of three sets each constructed by two in-phase pistons usually symmetrically disposed has a crank angle of 120°. FIG. 2(a) shows the relation of phases of a fundamental wave. With the configuration, each of the fundamental components generated by the pistons of the sets forms 120° in the crank angle, and the fundamental components cancel each other out. FIG. 2(b) shows the relation of phases of second harmonic waves. Each of the second harmonic components is generated with a phase having a crank angle of 120°×2=240°, that is, 120° from the other direction, so that the second harmonic components cancel each other out. That's why the in-line 6-cylinder engine has a small amount of vibration. The alternately long and short dash line in the diagram shows the phase of vibration generated by the third piston set. The configuration of the in-line 4-cylinder engine in which the second harmonic vibration is emphasized in theory corresponds to the pulse inversion. The configuration of the in-line 6-cylinder engine in which vibrations of not only the fundamental wave but also the second harmonic wave are canceled out in theory correspond to the method of the present invention.

Generally, with respect to vibration of an in-line 2N cylinder engine where N is an integer of 3 or greater, the vibrations from the fundamental wave, that is, the first harmonic wave to the (N−1)th harmonic wave are cancelled out in theory. When the case is replaced with the case of ultrasonic imaging of the present invention, transmitting/receiving operation is performed N times by using transmission pulse waves having a common envelope signal while varying the carrier waves in phase by 360°/N from one wave to the next, and N pieces of echo signals obtained are summed, so that components of the fundamental wave to the (N−1)th harmonic wave of the echo signal scattered by a linear scatterer whose change in short time can be ignored are simultaneously cancelled out.

On the other hand, the phase of the echo signal generated by being scattered by the microbubble contrast medium is influenced by the amplitude of the envelope due to its strong nonlinear resonance characteristic and does not have a predetermined relation with the phase of the transmission signal carrier wave. Consequently, even if three echo signals obtained by performing the transmitting/receiving operation three times while varying the phase of the transmission pulse carrier wave by 120° each time are summed, in the case of the echo signals generated by being scattered by the microbubbles for contrast, components which are not cancelled out remain. Since the remaining echo signal components reflect only the existence of the microbubble contrast medium, ultrasonic imaging in which the contrast medium is clearly distinguished from the soft tissue can be realized.

The characteristics of the ultrasonic imaging method according to the present invention will be described hereinbelow.

(1) An ultrasonic imaging method for transmitting/receiving ultrasonic pulses to/from a living body in which microbubbles for contrast are introduced, and forming a contrast image of the inside of the living body by the microbubbles for contrast, comprising: a step of performing transmitting/receiving operations N times (N=an integer of three or greater) by using transmission pulse waves having different waveforms under the same transmission/reception wave focus condition; a step of summing N pieces of time-series reception echo signals obtained by the transmitting/receiving operations of N times to obtain a summed signal, thereby suppressing transmission/reception sensitivity to components from a fundamental wave to the (N−1)th-order harmonic wave of an ultrasonic echo signal from a soft tissue in the living body, extracting signals resulted from the microbubbles for contrast, and forming the contrast image; and a step of displaying the contrast image.

(2) In the ultrasonic imaging method (1), an amplitude of a summed signal of the N pieces of transmission pulse waves is smaller than an amplitude of each of the N pieces of transmission pulse waves.

(3) In the ultrasonic imaging method (1), the N pieces of transmission pulse waves have a common envelope signal, and carrier waves vary in phase by 360°/N from one wave to the next.

(4) In the ultrasonic imaging method (1), N is three, the three transmission pulse waves have a common envelope signal, and carrier waves vary in phase by about 120° from one wave to the next.

(5) In the ultrasonic imaging method (1), an image of the living body is formed from the amplitude of the summed signal of N pieces of time-series reception echo signals obtained by the N times of transmitting/receiving operations and is displayed with luminance in which the amplitude is reflected.

(6) In the ultrasonic imaging method (1), an image of the living body is formed from the amplitude of a weighted sum signal according to a combination of a plurality of sets of weights of the N pieces of time-series reception echo signals obtained by the N times of transmitting/receiving operations, and is displayed with luminance in which the amplitude is reflected.

(7) In the ultrasonic imaging method (6), the amplitude of the weighted sum signal is displayed so as to be superimposed in a display color which varies.

(8) In the ultrasonic imaging method (6), at least one of the plurality of sets of combinations of weights is constructed to suppress the transmit/receive sensitivity to the fundamental wave component and the even-order harmonic wave component of the ultrasonic echo signal from the soft tissue and to obtain the transmit/receive sensitivity to the ultrasonic wave echo signal from the microbubbles for contrast, and at least another set is constructed to obtain transmit/receive sensitivity to the ultrasonic echo signal from the soft tissue.

(9) An ultrasonic imaging method for transmitting/receiving ultrasonic pulses to/from a living body in which microbubbles for contrast are introduced and forming a contrast image of the inside of the living body by using the microbubble for contrast, including: a step of performing transmitting/receiving operations N times (N=an integer of three or greater) by using transmission pulse waves having a common envelope signal under the same transmission/reception wave focus condition while varying the carrier waves in phase by 360°/N from one wave to the next; and a step of summing N pieces of time-series reception echo signals obtained by the N times of transmitting/receiving operations to obtain a summed signal, thereby forming the contrast image.

(10) In the ultrasonic imaging method (9), N is three, the three transmission pulse waves have a common envelope signal, and carrier waves vary in phase by about 120° from one wave to the next.

BRIEF DESCRIPTION OF DRAWINGS

FIGS. 4(a) to 4(d) are diagrams showing an example of echo signals from a point reflector in a living body soft tissue having a nonlinear propagation characteristic, obtained by the present invention, FIGS. 5(a) to 5(c) are diagrams showing an example of echo signals from a point reflector in a living body soft tissue having a nonlinear propagation characteristic, obtained by the pulse inversion, FIGS. 7(a) to 7(f) are diagram showing waveforms of the echo signals scattered by the microbubbles for contrast obtained by the present invention after passage of a bandpass filter, FIGS. 9(a) to 9(f) are diagrams showing waveforms of echo signals scattered by microbubbles for contrast obtained by the pulse inversion after passage of a bandpass filter, FIGS. 10(a) to 10(d) are diagrams showing an example of echo signals by a point reflector in a living body soft tissue, obtained by intentionally multiplexing a second harmonic wave on a transmission pulse wave in the present invention, FIGS. 12(a) to 12(f) are diagrams showing waveforms of echo signals scattered by microbubbles for contrast, obtained by intentionally multiplexing a second harmonic wave on a transmission pulse wave in the present invention, after passage through a bandpass filter, FIG. 14 is a diagram showing phase error dependency of the adder output signal amplitudes, of echo signals from the point reflector in the living body soft tissue, obtained when there is an error in the phases of transmission wave pulses in the present invention, and FIGS. 15(a) to 15(c) are diagrams showing an example of transmission waveforms in the present invention.

BEST MODE FOR CARRYING OUT THE INVENTION

An embodiment of the present invention will be described hereinbelow with reference to the drawings.

Figure 1A:
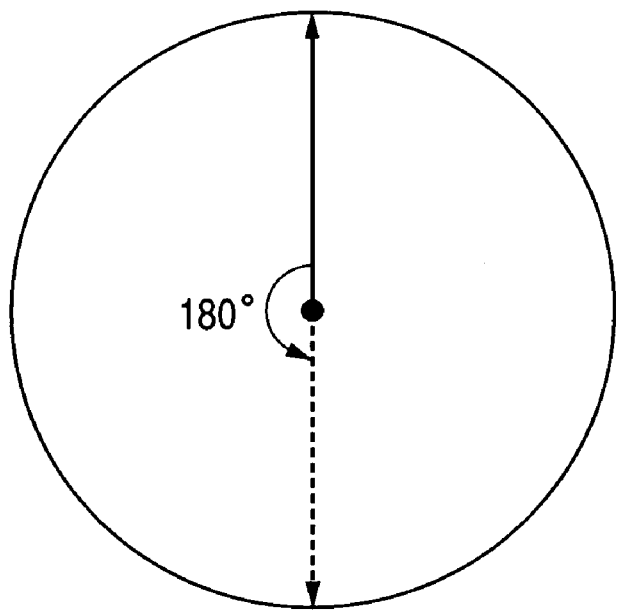
FIGS. 1(a) to 1(b) are diagrams illustrating the principle of the pulse inversion.
Figure 1B:
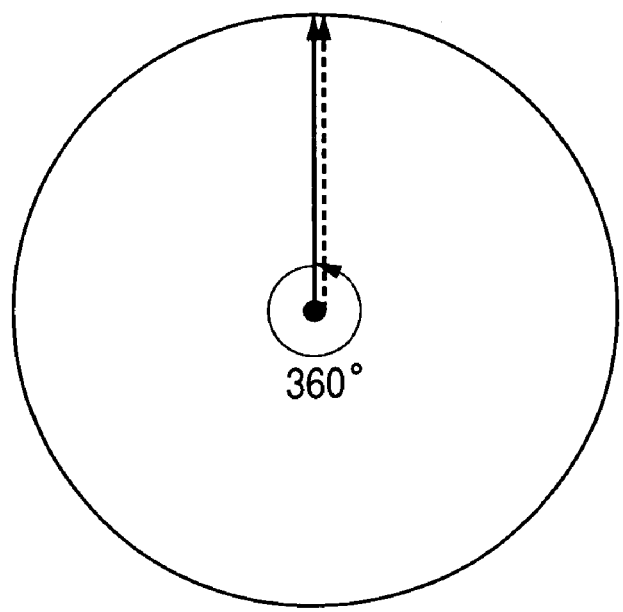
Figure 2A:
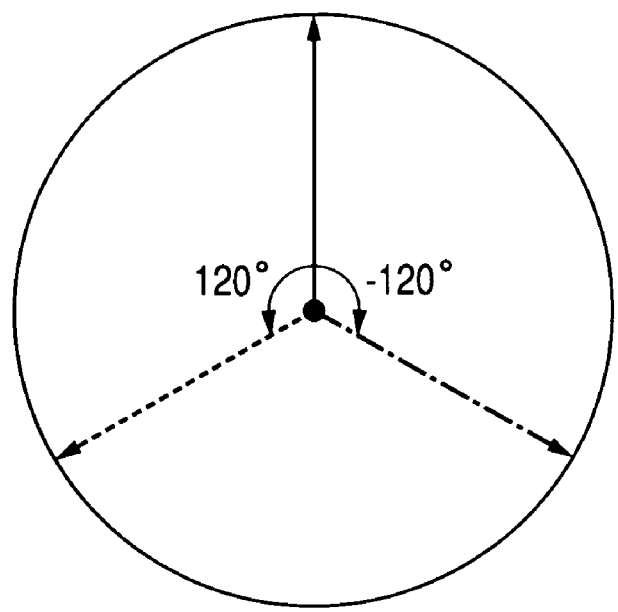
FIGS. 2(a) to 2(b) are diagrams illustrating the principle of a three-pulse method of the present invention.
Figure 2B:
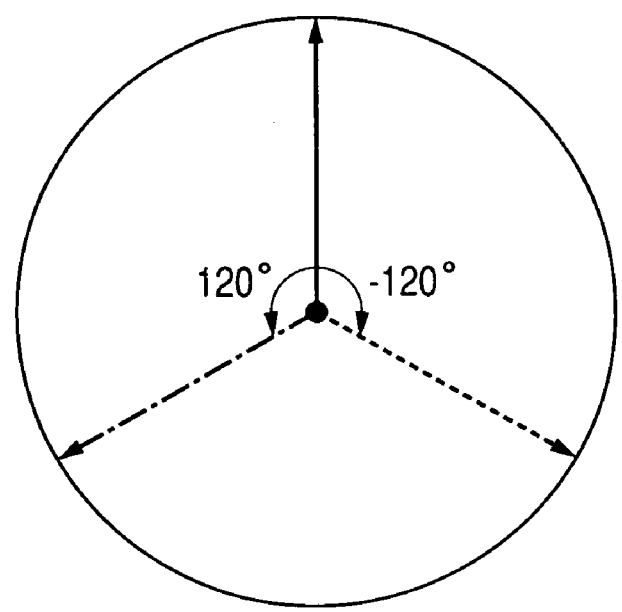
Figure 3:
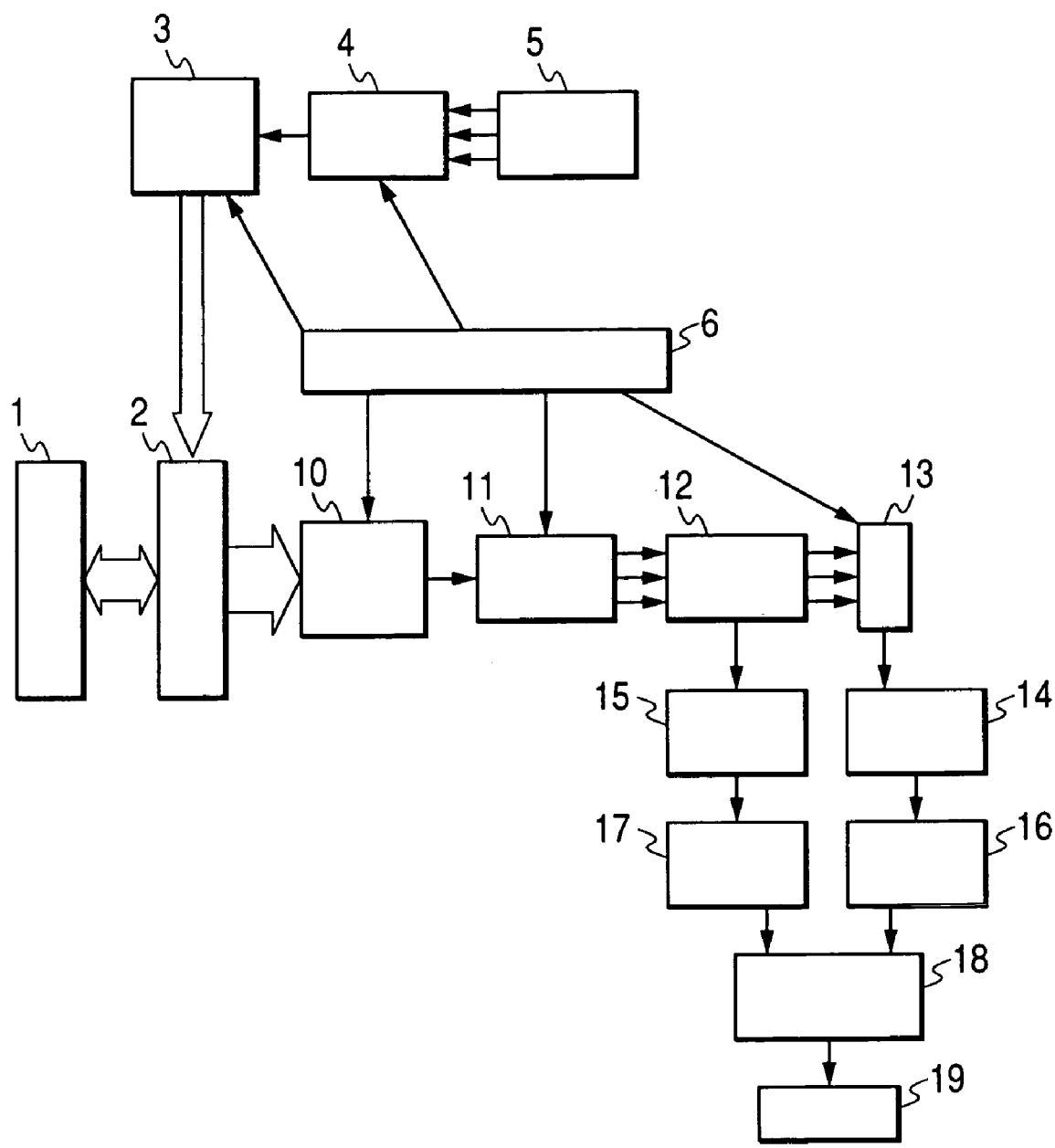
FIG. 3 is a block diagram showing the configuration of an ultrasonic imaging device in the embodiment of the present invention.

FIG. 3 is a typical example of a block diagram of an ultrasonic imaging device constructed to carry out the present invention. Elements constructing an ultrasonic probe 1 are connected to a transmit beamformer 3 and a receive beamformer 10 via transmit/receive switches 2. The transmit beamformer 3 generates a signal which becomes an ultrasonic pulse having directivity when transmitted via the elements by using waveforms selected and read from a transmit waveform memory 5 by a transmit waveform selector 4 under control of a transmit/receive sequence controller 6. The signal is converted to ultrasonic pulses by the elements of the ultrasonic probe 1, and the ultrasonic pulses are transmitted to the living body. Ultrasonic echo signals reflected or scattered in the living body and returned to the ultrasonic probe 1 are received by the elements and converted to electric signals.

In the receive beamformer 10, under control of the transmit/receive sequence controller 6, to obtain reception sensitivity having directivity, delay time is given to each of receive signals, and the receive signals are summed to each other. A time-series signal obtained by delay summation is once written in one of banks in a receive waveform memory 12 selected by a receive waveform selector 11 under control of the transmit/receive sequence controller 6. After time-series signals to be summed to each other are ready, they are read and summed to each other by an adder 13. An adder output signal passes through a bandpass filter 14 for eliminating noise components and is converted to an envelope signal by an envelope detector A 16. The envelope signal is input to a scan converter 18.

On the other hand, part of the time series signals written in the receive waveform memory 12 is read, passes through a bandpass filter 15 for removing noise components without being summed to each other, and is converted to an envelope signal by an envelope detector B 17. The envelope signal is input to the scan converter 18. The scan converter 18 properly multiplexes a plurality of signals received, and generates/controls the signals so as to display a two-dimensional or three-dimensional image on a display 19.

As shown in FIG. 15, three ultrasonic pulse waveforms ((a), (b), and (c) in the diagrams) having a common envelope signal and whose carrier waves vary in phase by about 120° from one wave to another are written in the transmit waveform memory 5. FIGS. 4(a), 4(b), and 4(c) show signals written in the banks in the receive waveform memory 12 when a sequence of selecting one of the three ultrasonic pulse waveforms by the transmit waveform selector 4 and transmitting/receiving the selected one is executed three times. For simplicity, a receive echo signal generated when a transmit ultrasonic pulse propagates a living body soft tissue and is reflected by a point reflector is calculated by numerical value calculation simulation. It is assumed that the carrier wave frequency is 2 MHz. FIG. 4(d) shows an output signal obtained when the signals of FIGS. 4(a) to 4(c) are input to the adder 13. Since the transmit ultrasonic pulse nonlinearly propagates the living body soft tissue, the signals of FIGS. 4(a) to 4(c) include not only the fundamental wave component but also the second harmonic component. In the adder output result of FIG. 4(d), as estimated from the principle of the present invention, the fundamental wave components cancel each other out and, moreover, the second harmonic wave components also cancel each other out, so that the signal amplitude is almost zero.

For comparison, FIG. 5 show results in the case of using the pulse inversion. In this case, two kinds of ultrasonic pulse waves having a common envelope signal and whose carrier waves vary in phase by about 180° from one wave to another are written in the transmit waveform memory 5. One of the ultrasonic pulse waveforms is selected and transmitted/received by the transmit waveform selector 4. FIGS. 5(a) and 5(b) show signals written in the banks in the receive waveform memory 12 when the sequence is executed twice while changing the waveforms. FIG. 5(c) shows an output signal of the adder 13, which is obtained at that time. In the resultant signal, the fundamental wave components cancel out each other but the second harmonic wave components rather enhance each other. The signal is called a tissue harmonic signal which has an advantage that a high acoustic S/N ratio is obtained at the time of drawing a living body soft tissue. However, in the case of drawing only a distribution or kinetics of a contrast medium so as to be clearly separated from a soft tissue, the tissue harmonic signal becomes the maximum factor of disturbing the drawing.

Next, a receive echo signal by the contrast microbubbles in the same transmit/receive sequence as that in the case of FIGS. 4 and 5 will be shown. FIGS. 6 and 8 show, as an example, results of obtaining receive echo signals generated by scattering of mirobubbles each having a radius of 1.5 μm by a numerical value calculation simulation, and FIGS. 7 and 9 show input/output signals of the bandpass filter 14 at that time. The scale of the vertical axis proportional to the acoustic pressure is common in FIGS. 6, 7, 8, and 9.

Figure 6A:
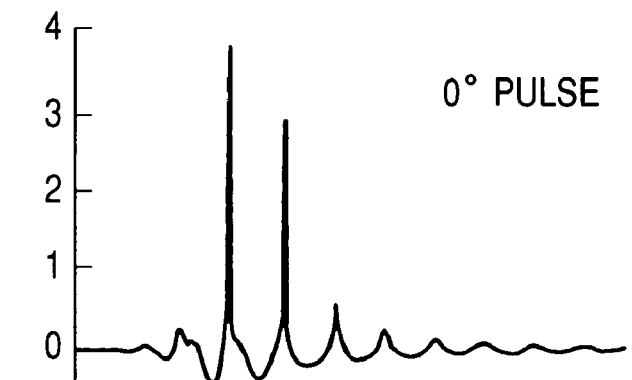
FIGS. 6(a) to 6(d) are diagrams showing an example of the echo signals scattered by microbubbles for contrast, obtained by the present invention.
Figure 6B:
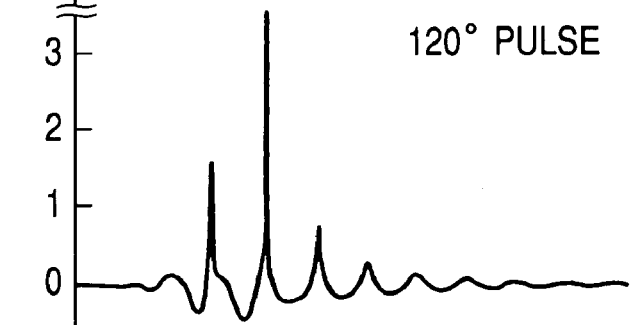
Figure 6C:
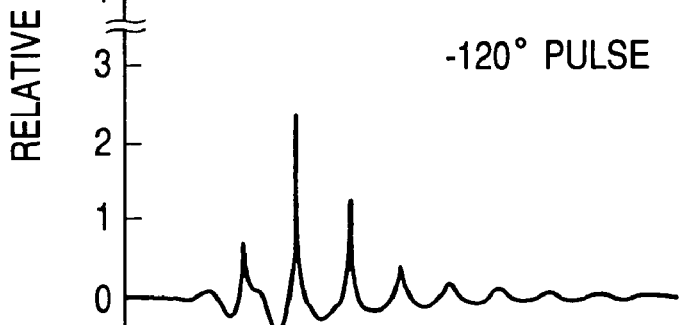
Figure 6D:
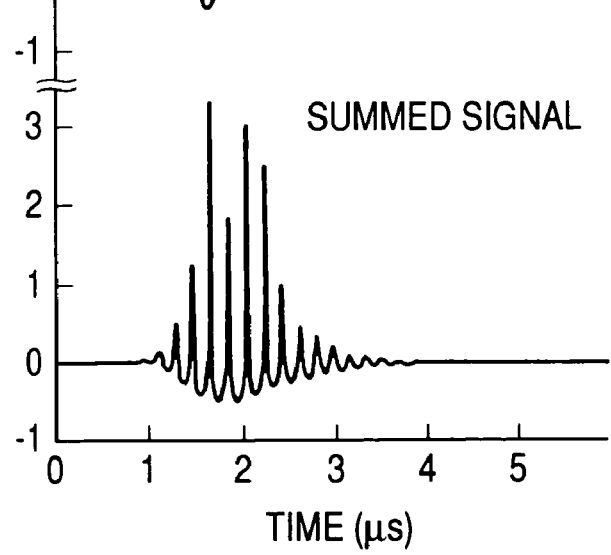
Figures 8A, 8B, 8C:
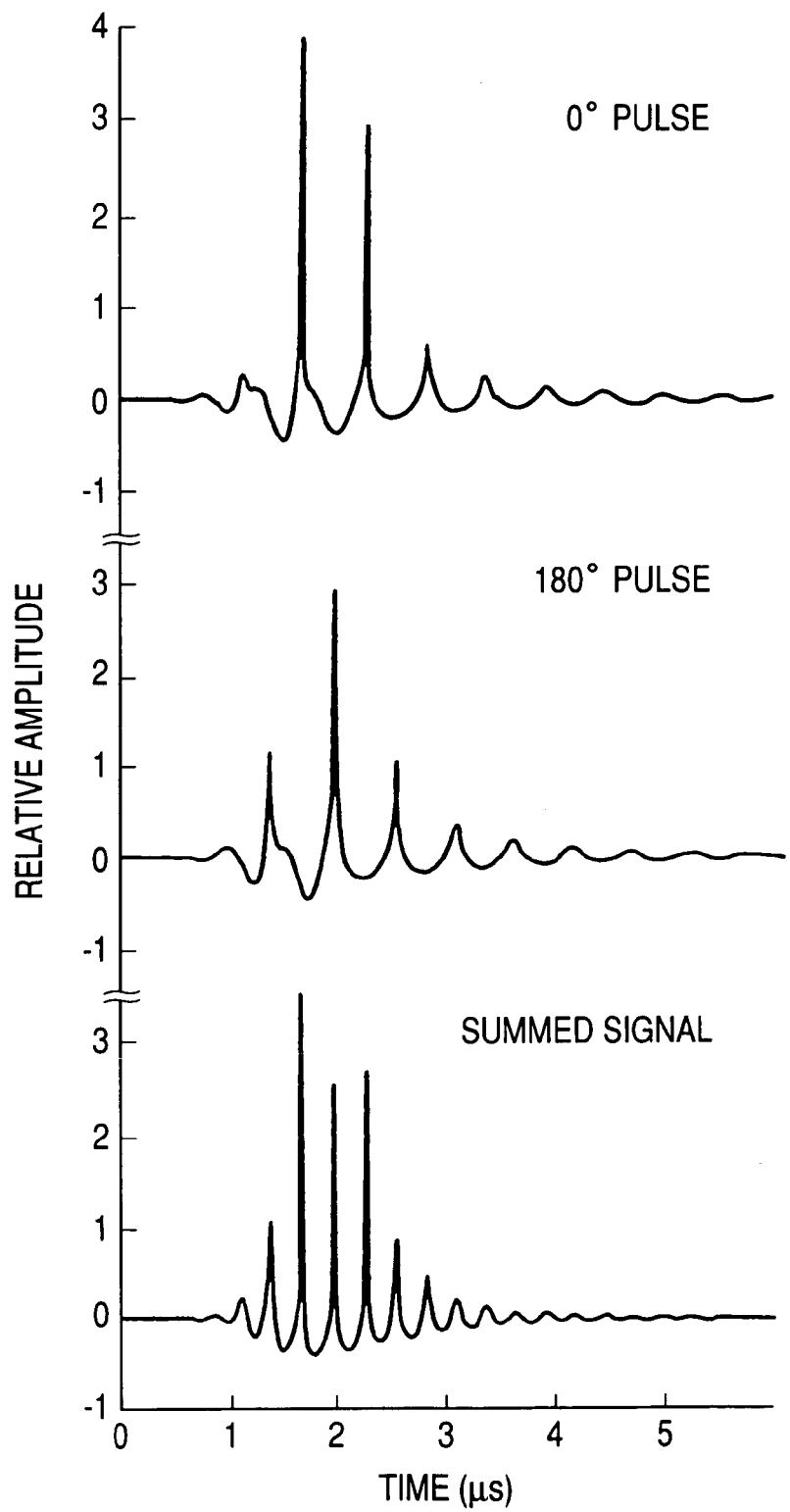
FIGS. 8(a) to 8(c) are diagrams showing an example of echo signals scattered by the microbubbles for contrast, obtained by the pulse inversion.

Each of the correspondences will be described. FIGS. 6(a), 6(b), and 6(c) show signals written in banks in the receive waveform memory 12 in a transmit/receive sequence when the present invention is carried out in a manner similar to the case of FIG. 4. Each of FIGS. 6(d) and 7(a) shows an output signal of the adder 13 obtained at that time, that is, an input signal of the bandpass filter 14. FIGS. 7(b), 7(c), 7(d), 7(e), and 7(f) show output signals of the bandpass filter 14 when the pass band center frequency is set to the fundamental wave frequency (2 MHz), 1.5-times harmonic frequency (3 MHz), second harmonic frequency (4 MHz), 2.5-times harmonic frequency (5 MHz), and third harmonic frequency (6 MHz), respectively. FIG. 8 show signals written in banks in the receive waveform memory 12 in a transmit/receive sequence when the pulse inversion is carried out in a manner similar to the case of FIG. 5. Each of FIGS. 8(c) and 9(a) shows an output signal of the adder 13 obtained at that time, that is, an input signal of the bandpass filter 14. FIGS. 9(b), 9(c), 9(d), 9(e), and 9(f) show output signals of the bandpass filter 14 when the pass band center frequency is set in a manner similar to the case of FIG. 8.

Naturally, signals resulted from the microbubbles including many second harmonic wave components are obtained from the 1.5-times harmonic waves as shown in FIGS. 9(c) and 9(d) by the pulse inversion inherently devised to emphasize the second harmonic component in the echo signal. However, it is noteworthy that, by the transmit/receive sequence of the present invention devised to cancel out components generated by nonlinear propagation or the like in the second harmonic component in the echo signal, as shown in FIGS. 7(d), 7(e), and 7(f), a signal having a sufficient amplitude resulted from the microbubbles including many the second to third harmonic components is obtained. The origin of the unique and useful phenomenon is that the microbubble is a resonator having large nonlinearity, generally speaking, the microbubble has a response characteristic in which delay time depends on amplitude. Specifically, even if there is nonlinearity among input/output acoustic pressures, if the delay response time does not have dependency on amplitude, the second harmonic component in an output signal is canceled out as shown in FIG. 4(d). On the other hand, a simple linear resonator is out of the question since the second harmonic component itself is not generated.

On the basis of the principle, the transmit/receive sequence according to the invention also has an advantage that even if the second harmonic component is intentionally multiplexed on a transmission pulse waveform, while canceling out the second harmonic component, a signal having a sufficient amplitude resulted from the microbubbles for contrast is obtained. By intentionally multiplexing the second harmonic component on an ultrasonic transmit waveform, vibration, growth, and collapse of microbubbles in a living body or a liquid can be emphasized or, on the contrary, suppressed (reference: IEEE Transactions on Ultrasonics, Ferroelectrics, and Frequency Control, vol. 43, no. 6, pp. 1054-1062). The second harmonic multiplex transmit wave is also considered to be useful also in the case of ultrasonic imaging using the microbubbles for contrast.

FIGS. 10, 11, and 12 show examples of an echo signal obtained in the case where a second harmonic component is intentionally multiplexed on the transmit pulse waveform.

FIGS. 10(a), 10(b), and 10(c) show signals written into the banks in the receive waveform memory 12 when a sequence of selecting one of the three ultrasonic pulse waveforms by the transmit waveform selector 4 and transmitting/receiving the selected one is executed three times while varying the waveform. The three ultrasonic pulse waveforms have a common envelope signal in the transmit waveform memory 5 and whose fundamental waves as carrier waves and second harmonic waves vary in phase by 120° from one wave to the next. FIG. 10(d) shows an output signal of the adder 13 obtained at that time.

Figures 11A, 11B, 11C, 11D:
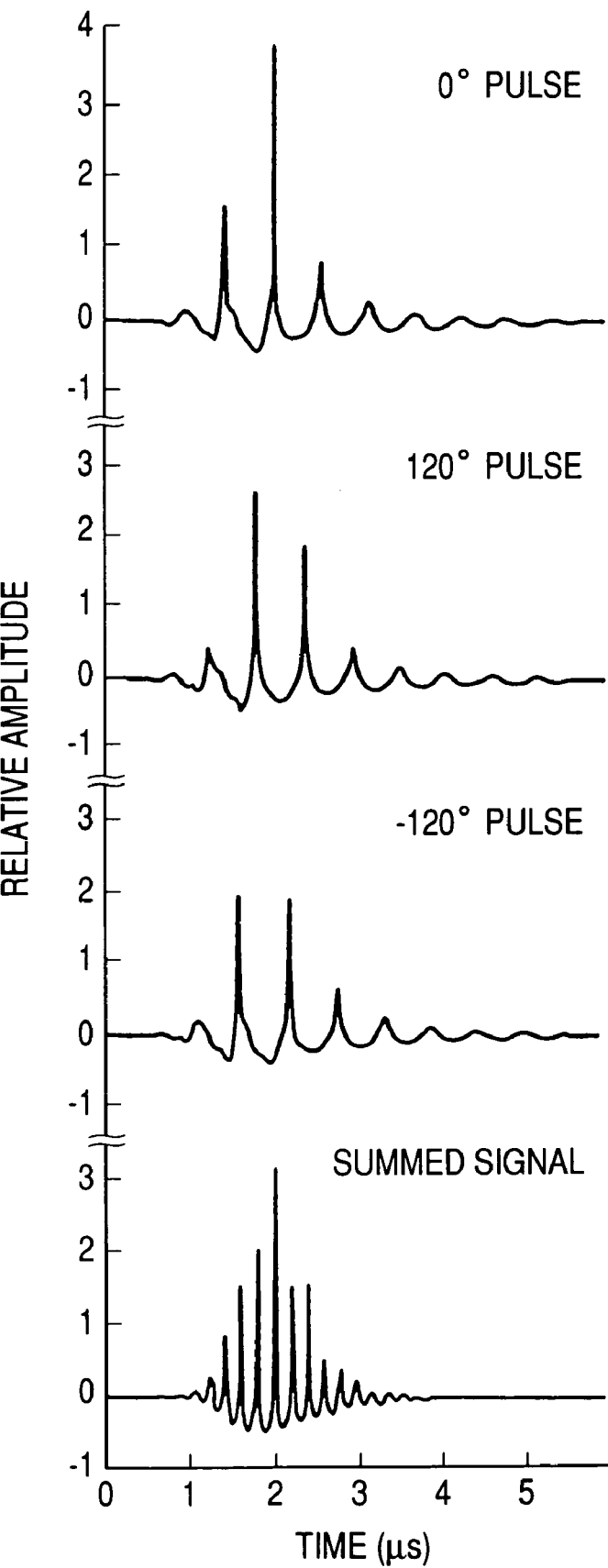
FIGS. 11(a) to 11(d) are diagrams showing an example of echo signals scattered by the microbubbles for contrast, obtained by intentionally multiplexing a second harmonic wave on a transmission pulse wave in the present invention.

A receive echo signal generated by scattering with the microbubbles for contrast is obtained in a manner similar to the case of FIG. 6. FIGS. 11(a), 11(b), and 11(c) show signals to be written in the banks in the receive waveform memory 12.

Each of FIG. 11(d) and FIG. 12(a) shows an output signal of the adder 13 obtained at that time, that is, an input signal of the band pass filter 14.

FIGS. 12(b), 12(c), 12(d), 12(e), and 12(f) show output signals of the bandpass filter 14 when the pass band center frequency is set in a manner similar to FIG. 8.

As obvious from FIG. 10(d), also in the case where the second harmonic component is intentionally multiplexed on the transmit pulse waveform, with respect to a receive echo signal generated by scattering by the point reflector, the second harmonic components of the input signal to the adder 13 cancel each other out in a manner similar to the second harmonic components generated by the nonlinear propagation in the case of FIG. 4, so that the adder output signal amplitude is almost zero. On the other hand, in a manner similar to FIG. 6, the receive echo signals generated by scattering by the microbubbles for contrast are not cancelled each other out by summing of the adder 13, and an output signal having a sufficient amplitude including the second and third harmonic components is obtained.

Figure 13A:
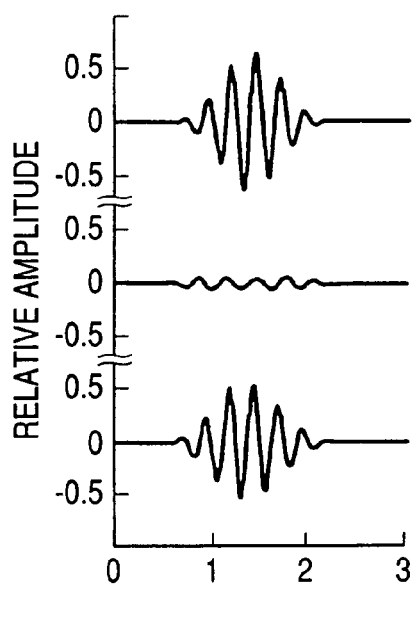
FIGS. 13(a) to 13(c) are diagrams showing an example of adder output signal waveforms of echo signals from a point reflector in a living body soft tissue, obtained when there is an error in phases of transmission wave pulses in the present invention.
Figure 13B:
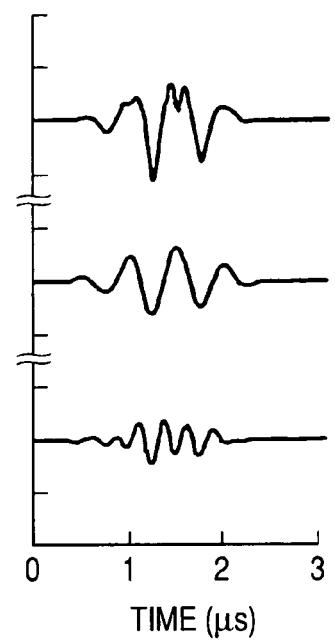
Figure 13C:
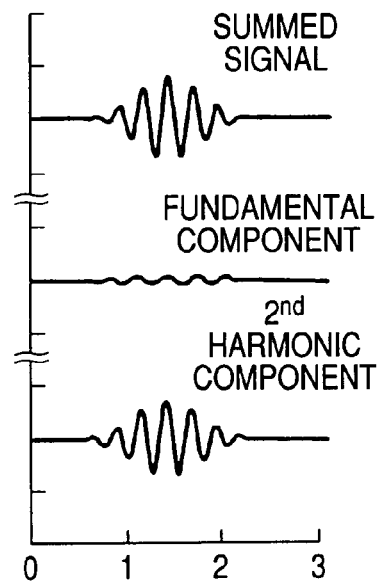

Further, an error range permissible to obtain the effects of the present invention of the phases of transmit pulse waves was examined. As examples, an output signal of the adder 13, that is, an input signal of the bandpass filter 14 in the case where the phase of the second transmit pulse wave is shifted by 20° and a filter output signal in the case where the pass band center frequency is adjusted to the fundamental wave and the second harmonic wave were obtained in a manner similar to the case of FIG. 4 and shown in FIGS. 13(b) and 13(c). For comparison, FIG. 13(a) shows the signal of the case of FIG. 5, that is, a signal in the case where the pulse inversion could be carried out without a phase error. FIG. 13(c) shows the case where the phase of the third transmit pulse wave was adjusted by being shifted by 10° in correspondence with a phase shift of 20° of the second transmit pulse wave so that the sum signal of three transmit pulse waves becomes zero.

When an envelope signal of the transmit pulse wave is written as A(t) as the function of time "t", first, second, and third transmit pulse signals P1(t), P2(t), and P3(t) can be written as follows when there is no phase error.

$$P1(t)=A(t)\sin\omega t \quad (1)$$

$$P2(t)=A(t)\sin(\omega t+2\pi/3) \quad (2)$$

$$P3(t)=A(t)\sin(\omega t-2\pi/3) \quad (3)$$

At this time, the following relation is satisfied.

$$P1(t)+P2(t)+P3(t)=0 \quad (4)$$

When the phase error φ occurs in the second pulse, the second pulse can be written as follows.

$$P2(t)=A(t)\sin(\omega t+2\pi/3+\phi) \quad (5)$$

When the third pulse is adjusted to satisfy the following equations, Equation (4) can be satisfied irrespective of the phase error φ.

$$P3(t)=A3(t)\sin(\omega t-2\pi/3+\phi/2) \quad (6)$$

$$A3(t)=2A(t)\cos(\pi/3+\phi/2) \quad (7)$$

FIG. 13(c) shows a result of making a such correction on the third pulse. The fundamental components in the output signal of the adder 13 can be cancelled each other out irrespective of a phase error in the second pulse.

When Equation (4) is satisfied, generally, when the sum signal of N pieces of pulse waveforms used for transmission is substantially zero, the fundamental wave components in signals obtained by summing N pieces of receive echo signals are cancelled each other out.

FIG. 14 shows a peak-to-peak value of the output signal amplitude of the adder 13 as a function of the phase error given to the second pulse. FIG. 14 shows the case ((a) in the diagram) of a signal amplitude normalized with a value in the case where the pulse inversion could be carried out without a phase error when a correction is not made on the third pulse, and the case ((b) in the diagram) where the correction is made. When the phase error reaches 20°, although the correction is made on the third pulse, a signal amplitude which is resulted from the nonlinear propagation in a soft tissue and is not resulted from the microbubble for contrast becomes the half or more of the conventional pulse inversion, and the effects of the present invention are not sufficiently displayed. From the result, it is desirable to set the phase error of the transmit pulse to about 10° or less in order to sufficiently obtain the effects of the invention.

As described above, by executing the present invention, a signal which does not include a signal component resulted not from the nonlinear propagation in a soft tissue or the like but resulted only from the microbubbles for contrast can be extracted from an echo signal.

Such a signal can be obtained as an output signal of the adder 13, further, a signal with improved S/N ratio is obtained as an output signal of the bandpass filter 14, and an output signal of the envelope detector A 16 is obtained as an envelope signal and is input as a signal indicative of a spatial distribution of the microbubbles for contrast into the scan converter 18. On the other hand, an envelope signal is obtained by the envelope detector B 17 from the signal whose S/N ratio is improved by passing a signal written in one of the banks of the receive waveform memory 12 through the bandpass filter 15. The obtained signal is input as a signal indicative of the position and the form of a soft tissue to the scan converter 18.

In the scan converter 18, the output signal of the envelope detector B 17 is used as a background, and an output signal of the envelope detector A 16 is multiplexed in a color tone different from that of the output signal of the envelope detector B 17 so as to be conveniently discriminated from the output signal. The resultant is displayed on the display 19. In such a manner, the distribution of the microbubbles for contrast in the body of a patient as an object of a test can be displayed by a two-dimensional or three-dimensional image so as to be more easily understood.

Although the case where a signal written in one of the banks of the receive waveform memory 12 is used as it is as a signal indicative of the position and the form of a soft tissue has been described in the foregoing embodiment, generally, a summed signal obtained by properly weighting signals written in three banks in the receive waveform memory 12 can be used.

Although the embodiment using three transmit pulse waves has been specifically described in the above description, as in the description of the principle, the present invention can be also carried out by using N pieces (N=an integer of three or greater) of transmit pulse waves having a common envelope signal, varying the carrier wave in phase by 360°/N from one wave to the next, performing N times of transmitting/receiving operations, temporarily writing N pieces of echo signals obtained by the transmitting/receiving operations into N pieces of banks in the receive waveform memory 12, and inputting read signals to the adder 13.

INDUSTRIAL APPLICABILITY

As described above, the present invention can provide an image for diagnosis having a high S/N ratio sufficient to make a definite diagnosis on the basis of a contrast echo image obtained by extracting signals resulting only from microbubbles for contrast, which do not include signal components resulting from nonlinear propagation and the like in a soft tissue from an echo signal. Consequently, usability for medical diagnosis of an apparatus to which the invention is applied is extremely high and, therefore, the significance of the present invention in industries supporting medial diagnosis is also great.

The invention claimed is:

1. An ultrasonic imaging device for transmitting/receiving ultrasonic pulse to/from a living body in which microbubbles for contrast are introduced, and forming a contrast image of the inside of the living body, comprising:
   a transmit beamformer for generating a transmit pulse;
   a receive beamformer for generating a time-series reception echo signal with adding receive signals, to each of which a delay time is given for generating receiving sensitivity having directivity;
   an adder for summing the time-series reception echo signals; and
   a transmit/receive sequence controller for controlling the transmit beamformer and the receive beamformer;
   wherein the transmit/receive sequence controller controls the transmit beamformer and the receive beamformer to perform transmitting/receiving operations N times (N=an integer of three or greater) by controlling N pieces of transmission pulse waves having a common envelope signal and different waveforms under a transmission/reception wave focus condition, and controlling carrier waves of the transmission pulse waves so to vary in phase by 360°/N from one wave to a next wave, and receiving returned ultrasonic waves as N pieces of the time-series reception echo signals; and
   wherein said adder sums the N pieces of the time-series reception echo signals so at to output an output signal as a signal indicative of a spatial distribution of the microbubbles.

2. The ultrasonic imaging device according to claim 1, wherein the adder includes a band pass filter for eliminating noise components and outputting said signal indicative of the spatial distribution of the microbubbles as the output signal.

3. The ultrasonic imaging device according to claim 1, wherein the output signal of the adder obtains transmission/reception sensitivity to an ultrasonic echo signal from the microbubbles with suppressing transmission/reception sensitivity to components form a fundamental wave to a harmonic wave of the ultrasonic echo signal from a soft tissue in the living body.

4. The ultrasonic imaging device according to claim 3, wherein the components to be suppressed are the components from the fundamental wave to the (N−1)th-order harmonic wave of an ultrasonic echo signal from the soft tissue in the living body.

5. The ultrasonic imaging device according to claim 1, wherein an amplitude of a sum signal of N pieces of transmission pulse waves is smaller than an amplitude of each of the N pieces of transmission pulse waves.

6. The ultrasonic imaging device according to claim 1, wherein a signal indicative of a position and a form of the soft tissue in the living body is obtained based on a part of the received signals.

7. The ultrasonic imaging device according to claim 6, wherein the signal indicative of the position and the form of the soft tissue in the living body is obtained from a part of the time-series reception echo signals.

* * * * *